United States Patent
Stecker et al.

(10) Patent No.: US 8,889,920 B2
(45) Date of Patent: Nov. 18, 2014

(54) PROCESS FOR PREPARING 4-ISOPROPYLCYCLOHEXYLMETHANOL

(75) Inventors: Florian Stecker, Mannheim (DE); Ulrich Griesbach, Mannheim (DE); Martin Bock, Hannover (DE); Lucia Königsmann, Stuttgart (DE)

(73) Assignee: BASF SE, Ludwigshafen (DE)

(*) Notice: Subject to any disclaimer, the term of this patent is extended or adjusted under 35 U.S.C. 154(b) by 469 days.

(21) Appl. No.: 13/025,528

(22) Filed: Feb. 11, 2011

(65) Prior Publication Data

US 2011/0207968 A1  Aug. 25, 2011

Related U.S. Application Data

(60) Provisional application No. 61/303,679, filed on Feb. 12, 2010.

(51) Int. Cl.
C07C 43/30 (2006.01)
C25B 3/02 (2006.01)
C07C 29/19 (2006.01)

(52) U.S. Cl.
CPC . *C25B 3/02* (2013.01); *C07C 29/19* (2013.01); *C07C 2101/14* (2013.01); *C07B 2200/09* (2013.01)
USPC ........... 568/831; 568/592; 568/814; 205/449; 205/452

(58) Field of Classification Search
CPC ...... C25B 3/02; C07B 2200/09; C07C 29/19; C07C 2101/14
USPC .................. 568/592, 831, 814; 205/449, 452
See application file for complete search history.

(56) References Cited

U.S. PATENT DOCUMENTS

| | | | |
|---|---|---|---|
| 3,993,604 A | 11/1976 | Thomas et al. | |
| 4,539,081 A | 9/1985 | Degner et al. | |
| 4,694,111 A | 9/1987 | Gupta | |
| 4,814,510 A | 3/1989 | Degner et al. | |
| 4,847,425 A | 7/1989 | Degner et al. | |
| 5,507,922 A | 4/1996 | Hermeling et al. | |
| 6,441,255 B1 * | 8/2002 | Haas et al. | 568/881 |
| 6,822,124 B2 * | 11/2004 | Putter et al. | 568/497 |
| 7,666,813 B2 | 2/2010 | Hoefer et al. | |
| 2010/0152436 A1 | 6/2010 | Laar et al. | |
| 2011/0251439 A1 | 10/2011 | Mirk et al. | |

FOREIGN PATENT DOCUMENTS

| | | |
|---|---|---|
| DE | 2427609 A1 | 1/1975 |
| DE | 3644076 A1 | 7/1988 |
| DE | 19904900 A1 | 12/1999 |
| DE | 102004011427 A1 | 9/2005 |
| DE | 102005029200 A1 | 12/2006 |
| EP | 0129795 A2 | 1/1985 |
| EP | 0293739 A1 | 12/1988 |
| EP | 0554564 A1 | 8/1993 |
| EP | 0638665 A1 | 2/1995 |
| KR | 20040072433 A | 8/2004 |
| WO | WO-2009/059941 A1 | 5/2009 |
| WO | WO-2009/059944 A1 | 5/2009 |
| WO | WO-2010/079035 A2 | 7/2010 |
| WO | WO-2011067386 A3 | 10/2011 |
| WO | WO-2011082991 A3 | 5/2012 |

OTHER PUBLICATIONS

Co-pending U.S. Appl. No. 13/260,650, filed Sep. 27, 2011.*
Vaudano et al., "Preparation of p-isopropylbenzaldehyde (p-cuminal) by Direct Electrochemical Oxidation of p-isopropyltoluene (p-cymene) in Methanolic Medium", *Electrochemica Acta*, vol. 46, pp. 875-880 (2001).
Loyson et al., "Mechanistic and Kinetic Aspects of the Direct Electrochemical Oxidation of 4-t-Butyltoluene", *S. Afr. J. Chem.*, vol. 55, pp. 125-131 (2002).
Loyson et al., "Kinetic Aspects of the Direct Electrochemical Oxidation of p-Xylene in Methanol Using Graphite Electrodes", *S. Afr. J. Chem.*, vol. 57, pp. 53-56 (2004).

* cited by examiner

*Primary Examiner* — Rosalynd Keys
(74) *Attorney, Agent, or Firm* — Drinker Biddle & Reath LLP

(57) ABSTRACT

The present invention relates to a process for preparing 4-isopropylcyclohexylmethanol (IPCHM) from para-cymene. The process for preparing 4-isopropylcyclohexylmethanol (IPCHM) comprises an electrochemical process for preparing a mixture of 4-isopropylbenzaldehyde dimethyl acetal and 4-(1-alkoxy-1-methylethyl)benzaldehyde dimethyl acetal, and intermediates passed through in the process, a hydrolysis step to form the corresponding benzaldehydes and a hydrogenation of this mixture to form 4-isopropylcyclohexylmethanol (IPCHM).

19 Claims, No Drawings

PROCESS FOR PREPARING 4-ISOPROPYLCYCLOHEXYLMETHANOL

RELATED APPLICATIONS

Pursuant to 35 U.S.C. §119(e), this application claims benefit of U.S. Provisional Patent Application Ser. No. 61/303,679, filed on Feb. 12, 2010.

The present invention relates to a process for preparing isopropylcyclohexylmethanol, wherein a compound of the para-cymene type is electrochemically methoxylated, the acetal formed is hydrolyzed to the aldehyde, and then the aldehyde is hydrogenated to the desired compound.

It is known that substituted benzaldehyde dimethyl acetals can be prepared directly by electrochemical methoxylation of the corresponding toluenes. P. Loyson, S. Gouws, B. Barton, M. Ackermann, S. Afr. J. Chem 2004, 57, 53-56 describe such a process. A disadvantage of the electrochemical side chain methoxylation of toluenes is that only toluenes substituted by electron-donating radicals such as tert-butyl, methyl or alkoxy can be methoxylated in yields of economic interest. Although radicals such as ethyl, isopropyl or isobutyl likewise have electron-donating action, the benzylic protons thereof can likewise be substituted by methoxy groups in a side reaction in the course of electrochemical conversion. For instance, p-cymene cannot be methoxylated smoothly to cuminaldehyde dimethyl acetal, as described in F. Vaudano, P. Tissot, Electrochimica Acta 2001, 46, 875-880, since the isopropyl group is always also partly methoxylated.

Substituted benzaldehyde dimethyl acetals and the parent aldehyde thereof are important intermediates, for example in the synthesis of odorants, for example cyclamenaldehyde, Lysmeral®, Silvial or 4-isopropylcyclohexylmethanol (IPCHM), which is sold under the Mayol® trade name.

EP 0 129 795 A2 describes a process for preparing substituted benzaldehyde dialkyl acetals by electrooxidation of correspondingly substituted alkyltoluenes, in which an electrolyte which comprises 50 to 90% by weight of a corresponding alkanol, 8.5 to 40% by weight of the alkyltoluene and 0.01 to 1.5% by weight of an acid containing HOBS groups is used.

EP 0 554 564 A1 discloses a process for preparing substituted benzaldehyde acetals, wherein the substituents of the aromatic have at least one benzylic hydrogen atom, by electrochemical oxidation of a corresponding benzyl ether in the presence of a corresponding alkanol, and in the presence of an auxiliary electrolyte, by electrolyzing in the acidic, neutral or weakly basic range.

EP 0 638 665 A1 discloses a process for preparing substituted benzaldehyde dialkyl acetals by electrochemical oxidation of correspondingly substituted toluene compounds, by oxidizing a substituted toluene compound in the presence of an alkanol and of an auxiliary electrolyte in an electrolysis cell, decompressing the resulting reaction solution outside the electrolysis cell to a pressure which is 10 mbar to 10 bar lower than the pressure in the electrolysis cell.

EP 0 293 739 discloses a process for preparing 4-isopropylcyclohexylmethanol (IPCHM) and the alkyl ethers thereof by ring hydrogenation in the presence of noble metals of group VIII of the periodic table, for example nickel, palladium, platinum, rhodium or ruthenium, preceding from 4-(1-alkoxy-1-methylethyl)benzaldehydes or the corresponding dialkyl acetals, which are obtainable by an electrochemical route from para-cymene. A disadvantage of this process is that the 4-(1-alkoxy-1-methylethyl)-benzaldehyde feedstock used has to be prepared in a separate process step from 4-(1-alkoxy-1-methylethyl)toluene, and this in turn in a separate process step from para-cymene.

WO 2010/079035 discloses a process for preparing 4-isopropylcyclohexylmethanol by catalytic hydrogenation over a fixed bed catalyst comprising ruthenium as active metal applied to a support comprising silicon dioxide as a support material.

DE 24 27 609 discloses alicyclic cyclohexylmethanols and the ethers or esters thereof, which have an isopropyl or isopropenyl radical in the 4 position, and the use thereof as odorants or flavorings. The document further discloses processes for preparing the compounds mentioned by catalytic hydrogenation of correspondingly unsaturated starting compounds. By way of example, the preparation of 4-isopropylcyclohexylmethanol by catalytic hydrogenation of cuminaldehyde in 1,2-dimethoxyethane as a solvent and in the presence of a ruthenium-carbon catalyst with a ruthenium content of 5% is described. The reaction was performed at a pressure of 100 atmospheres and at a temperature of 130° C., and afforded, after fractional distillation of the crude product, 4-isopropylcyclohexylmethanol in the form of a mixture of 70:30 parts by weight of the cis and trans isomers.

It was an object of the present invention to provide a simple process, useable for industrial scale preparation, for preparing 4-isopropylcyclohexylmethanol (IPCHM), which does not have the disadvantages of the known processes.

The object was achieved by converting, for example, a mixture of cuminaldehyde and 4-(1-alkoxy-1-methylethyl)benzaldehyde (alkoxycuminaldehyde), which can be obtained by electrochemical methoxylation of para-cymene and hydrolysis of the corresponding alkyl acetals, in the presence of noble metals of group VIII of the periodic table and in the presence of hydrogen.

The present invention thus provides a process for preparing 4-isopropylcyclohexylmethanol of the formula (I)

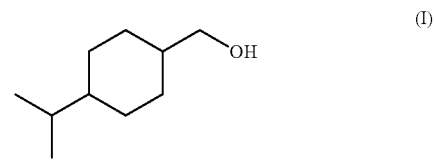

comprising the steps of a) electrochemical anodic methoxylation of at least one compound of the formula (II)

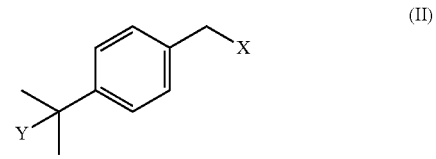

in which X is hydrogen or the —O—R radical and Y is hydrogen or the —O—$R_1$ radical, where R is methyl or —C(O)R', and R' and $R_1$ are each independently a straight-chain or branched alkyl radical having 1 to 6 carbon atoms, and/or the compound of the formula (III)

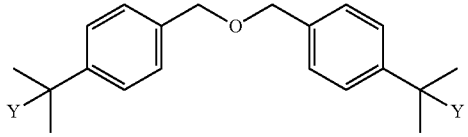

in which Y is as defined in formula (II), in an electrolysis solution comprising methanol, at least one conductive salt and optionally a further solvent or a plurality of different further solvents, to form at least one diacetal of the formula (IV)

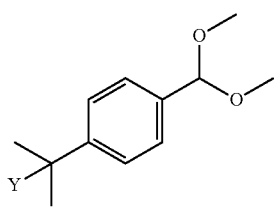

in which Y is as defined in formula (II), b) hydrolysis of the diacetal of the formula (IV) to form at least one aldehyde of the formula (V)

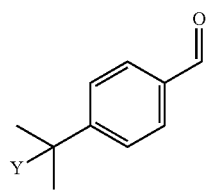

in which Y is as defined in formula (II), and c) hydrogenation of at least one aldehyde of the formula (V) to 4-isopropylcyclohexylmethanol of the formula (I) in the presence of hydrogen or a hydrogenous gas over a catalyst which comprises, as an active metal, at least one noble metal of group VIII of the periodic table on a support.

The desired end product of the process according to the invention is generally a mixture of cis- and trans-isopropylcyclohexylmethanol (IPCHM) of the formulae (Ia) and (Ib)

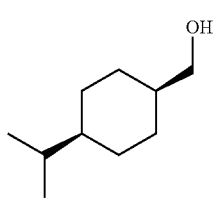

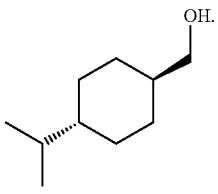

In the starting compound of the formula (II) in which R' and $R_1$ are each independently a straight-chain or branched alkyl radical having 1 to 6 carbon atoms, examples of useful alkyl radicals include methyl, ethyl, propyl, isopropyl, n-butyl, isobutyl, tert-butyl, sec-butyl, pentyl and hexyl.

The hydrogenation is performed in the presence of hydrogen or hydrogenous gas mixtures. Such gas mixtures may comprise, as well as hydrogen, gases such as nitrogen or hydrocarbonaceous reformer offgases, but not catalyst poisons such as carbon monoxide, hydrogen sulfide or other sulfur-containing gases. Preference is given to using pure hydrogen (purity≥99.9% by volume, particularly ≥99.95% by volume, especially ≥99.99% by volume).

As desired, the hydrogenation can be performed in a solvent or undiluted. Suitable solvents are, for example, alcohols such as methanol or ethanol, ethers such as tetrahydrofuran or dioxane, hydrocarbons such as pentane, and acids such as acetic acid. The reaction is preferably performed without solvent. The inventive hydrogenation can be performed continuously or batchwise.

The hydrogenation takes place in the presence of noble metals of group VIII of the periodic table, for example nickel, palladium, platinum, rhodium or ruthenium, preferably rhodium or ruthenium, more preferably ruthenium, and in the presence of hydrogen under pressure, especially under hydrogen pressures of 30-300 bar, preferably of 100 to 200 bar, at preferably relatively high temperatures, preferably at 50° C. to 250° C., more preferably at 80 to 200° C. and most preferably at 120 to 160° C.

In a preferred embodiment of the process according to the invention, the active metal used in the hydrogenation is at least one noble metal of group VIII of the periodic table, preferably rhodium and ruthenium, most preferably ruthenium, either alone or together with at least one further metal of transition groups IB (e.g. copper, silver, gold), VIIB (e.g. manganese, rhenium) or VIII of the periodic table of the elements (e.g. nickel, palladium, platinum) (CAS version). The noble metal is applied to a support which preferably comprises silicon dioxide and/or aluminum oxide, very particular preference being given to silicon dioxide as the support material. The amount of the active metal is <1% by weight, based on the total weight of the catalyst, and at least 60% by weight of the active metal is present in the shell of the catalyst down to a penetration depth of 200 μm, determined by means of SEM-EPMA (EDXS). Very particular preference is given to using a noble metal of group VIII of the periodic table alone, especially ruthenium.

In a further preferred embodiment of the process according to the invention, the active metal used in the hydrogenation is at least one noble metal of group VIII of the periodic table, preferably rhodium and ruthenium, either alone or together with at least one further metal of transition groups IB, VIIB or VIII of the periodic table of the elements, applied to a support comprising silicon dioxide as a support material, where the amount of the active metal is <1% by weight, based on the total weight of the catalyst, and at least 60% by weight of the active metal is present in the shell of the catalyst down to a penetration depth of 200 μm.

In a further preferred embodiment of the hydrogenation stage of the process according to the invention, the hydrogenation can be performed in the presence of the aldehydes of the formulae (Va) and (Vb), where $R_1$ is methyl, and also in the presence of the corresponding alcohols, 4-isopropylbenzyl alcohol and 4-(1-methoxy-1-methylethyl)-benzyl alcohol.

In a further preferred embodiment of the process according to the invention, a fixed bed catalyst which, based on the total weight of the finished catalyst, has an active content, especially a ruthenium content, of 0.1 to 0.5% by weight is used.

The starting compound used to perform the process according to the invention is the compound of the formula (II), preferably the compound para-cymene of the formula (IIa)

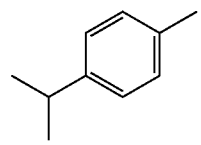
(IIa)

and/or 4-isopropylbenzyl compounds of the formula (IIb)

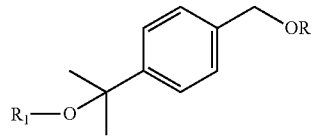
(IIb)

where $R_1$ in formula (IIb) is a straight-chain or branched alkyl radical having 1 to 6 carbon atoms, and R in formula (IIb) is methyl or —C(O)R', and R' is a straight-chain or branched alkyl radical having 1 to 6 carbon atoms, i.e., for example, 4-isopropylmethyl benzyl ether and/or the esters of the formula (IIb),
and/or di(4-isopropylbenzyl)ethers of the formula (III), preferably the di(4-isopropylbenzyl)ether of the formula (IIIa)

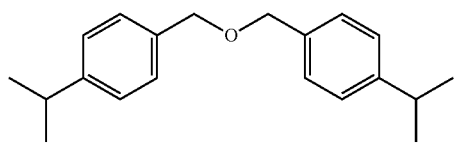
(IIIa)

and/or the di(4-isopropylbenzyl)ether of the formula (IIIb)

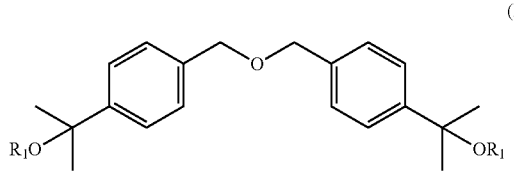
(IIIb)

in which $R_1$ is as defined in formula (IIb).

In the process according to the invention, the compounds mentioned can in principle each be used alone or else in the form of any mixtures of two or all three of the compounds mentioned. Particular preference is given to performing the electrochemical anodic methoxylation in the presence of the compound of the formula (IIa).

In a particularly preferred embodiment of the process according to the invention,
a) the electrochemical anodic methoxylation is performed with at least two compounds of the formulae (IIa), (IIb), (IIIa) and/or (IIIb)

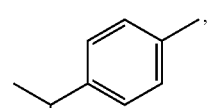
(IIa)

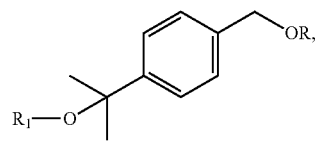
(IIb)

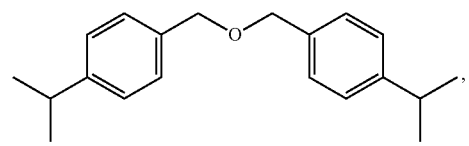
(IIIa)

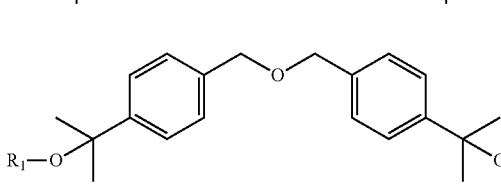
(IIIb)

such that a mixture of the diacetals of the formulae (IVa) and (IVb)

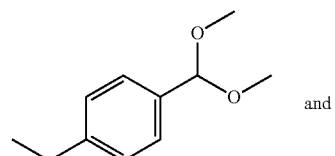
(IVa)
and

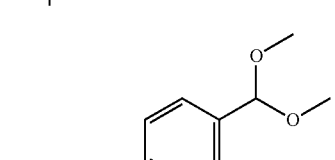
(IVb)

is formed, where $R_1$ in the formulae (IIb), (IIIb) and (IVb) is a straight-chain or branched alkyl radical having 1 to 6 carbon atoms, and R in formula (IIb) is methyl or —C(O)R', and R' is a straight-chain or branched alkyl radical having 1 to 6 carbon atoms, b) the mixture of the diacetals of the formulae (IVa) and/or (IVb) is hydrolyzed to form the aldehydes of the formulae (Va) and/or (Vb)

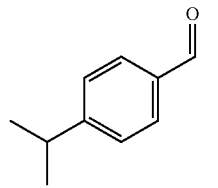
(Va)

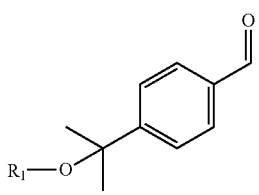
(Vb)

where $R_1$ is a straight-chain or branched alkyl radical having 1 to 6 carbon atoms, and c) the mixture of the aldehydes of the formulae (Va) and (Vb) is hydrogenated to 4-isopropylcyclohexylmethanol of the formula (I) in the presence of hydrogen or a hydrogenous gas over a catalyst which comprises, as an active metal, at least one noble metal of group VIII of the periodic table on a support.

Among the compounds of the formula (II) useable in accordance with the invention, preference is given especially to 4-isopropylbenzyl methyl ether of the formula (IIc)

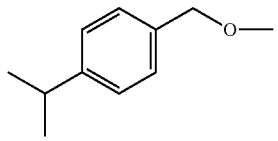
(IIc)

In the case of the esters of the formula (II) which are likewise useable, the R radical may be a straight-chain or branched alkyl radical having 1 to 6 carbon atoms, preferably methyl, ethyl, propyl or isopropyl, especially preferably methyl. A starting compound likewise preferred in accordance with the invention is accordingly the acetate of the formula (IId)

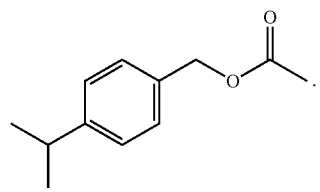
(IId)

In a particularly preferred embodiment of the process according to the invention, only para-cymene of the formula (IIa) is used as a starting material. In the course of the inventive electrochemical anodic methoxylation, it is possible first to form therefrom the compounds of the formula (II) mentioned, especially 4-isopropylbenzyl methyl ether of the formula (IIc)

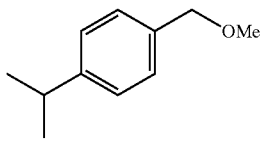
(IIc)

in which Me is methyl, and 4-(1-alkoxy-1-methylethyl)benzyl methyl ether of the formula (IIe)

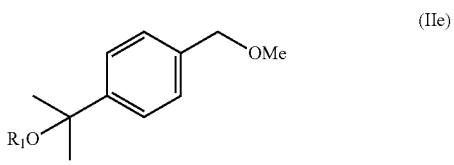
(IIe)

in which Me is methyl and $R_1$ is a straight-chain or branched alkyl radical having 1 to 6 carbon atoms, which then in turn, under the reaction conditions, react or are converted further to give the desired mixture of the alkyl acetals of the formulae (IVa) and (IVb)

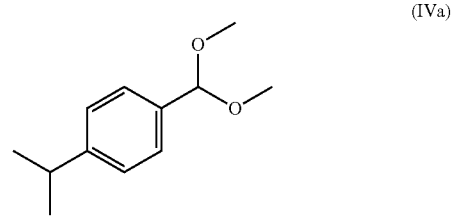
(IVa)

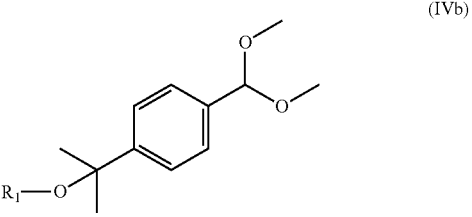
(IVb)

where $R_1$ is a straight-chain or branched alkyl radical having 1 to 6 carbon atoms.

4-Isopropylbenzyl methyl ether of the formula (IIc) is known and can be prepared as described, for example, in WO 2009059941 or WO 2009059944 by methoxymethylation of cumin with formaldehyde dimethyl acetal over a zeolite catalyst.

The preparation of substituted benzyl methyl ethers from alkylbenzenes in general (toluene, ethylbenzene, isobutylbenzene, cumin, tert-butylbenzene, etc.) by reaction with formaldehyde dimethyl acetal over a zeolite catalyst is described in DE 199 04 900. At low conversions (<30%), good product selectivities are obtained; at higher conversions, the reaction to give the diarylmethane predominates. Further means known to those skilled in the art for preparing the benzyl methyl ether of the formula (IId) are the methylation of 4-isopropylbenzyl alcohols or the reaction of 4-isopropylbenzyl halides with methanol or methoxides in a Williamson ether synthesis.

In a further embodiment of the process according to the invention, the di(4-isopropyl-benzyl)ether of the formula (III)

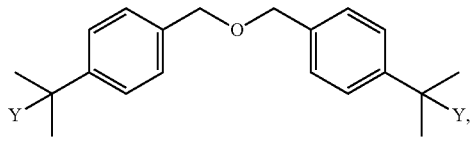

is used, in which Y is as defined above, either alone or as a mixture of the compounds of the formulae (IIIa) and (IIIb) or, as described above, in the form of a mixture with the further possible starting materials of the formula (II) or of the formulae (IIa) to (IIe). In this case, one equivalent of the dibenzyl ether of the formula (III) forms two equivalents of 4-isopropylbenzaldehyde dimethyl acetal of the formula (IV).

The dibenzyl ether of the formula (III) can be prepared, for example, by reacting the correspondingly substituted benzyl alcohol of the formula (IX')

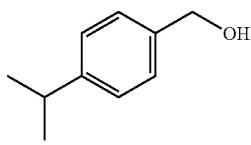

with the correspondingly substituted benzyl halide of the general formula (X)

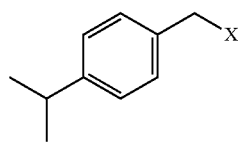

in which X is a halogen from the group of chlorine, bromine and iodine. Usually, the alcohols are deprotonated in the presence of bases (Fileti, Gazz. Chim. Ital. 1884, 14, 498-501). The ether synthesis can also be performed by acid-catalyzed condensation of two molecules of benzyl alcohol (Fileti, Gazz. Chim. Ital. 1882, 12, 501; F. Shirini, M. A. Zolfigol, K. Mohammadi, Phosphorus, Sulfur Silicon Relat. Elem. 2003, 178 (11), 2357-2362). There are numerous further examples of this reaction in the literature.

The di(4-isopropylbenzyl)ether of the formula (III) can also be prepared by functionalization of unsubstituted dibenzyl ether by relevant processes which are known to those skilled in the art, such as electrophilic aromatic substitution or Friedel-Crafts alkylation.

The occurrence of alkylbenzyl methyl ethers as intermediates of the electrochemical methoxylation of alkyltoluenes, for instance as intermediates in the methoxylation of p-tert-butyltoluene or p-xylene, is described in P. Loyson, S. Gouws, B. Zeelie, S. Afr. J. Chem., 2002, 55, 125-131 and P. Loyson, S. Gouws, B. Barton, M. Ackermann, S. Afr. J. Chem., 2004, 57, 53-56. The entry of the first methoxy group is the rate-determining step, which proceeds only with a moderate yield as a result.

In the electrochemical methoxylation of the dibenzyl ether of the formula (III), the benzaldehyde dimethyl acetal of the formula (IVa) or (IVb) is obtained directly, passing through the dibenzyl ether bismethoxylation intermediate (IX). However, this is not stable under the reaction conditions and reacts with methanol with release of water to give the compound of the formula (IVa) or (IVb).

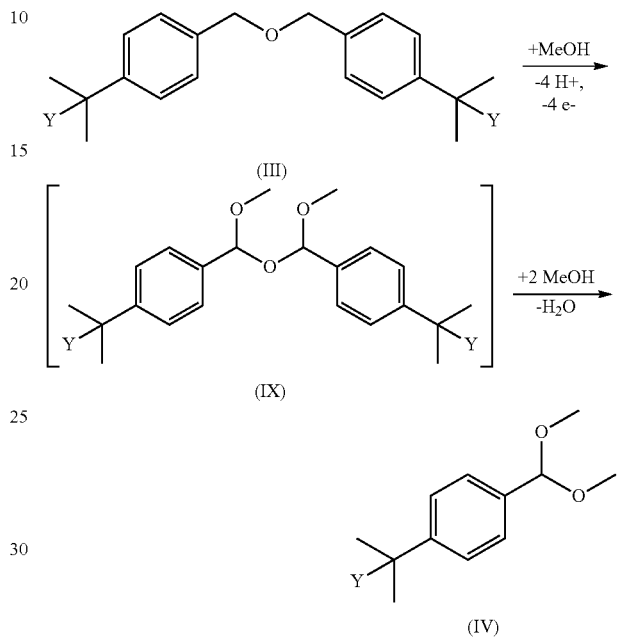

In which Y is hydrogen or the —O—$R_1$ radical, where $R_1$ is a straight-chain or branched alkyl radical having 1 to 6 carbon atoms.

In the process according to the invention, the electrolysis solution comprises, as well as the starting materials of the formulae (II) and/or (III) selected, at least methanol and at least one conductive salt.

The conductive salts which may be present in the electrolysis solution are generally alkali metal salts, tetra($C_1$- to $C_6$-alkylammonium) salts, preferably tri($C_1$- to $C_6$-alkyl)methylammonium salts. Useful counterions include sulfate, hydrogensulfate, alkylsulfates, arylsulfates, alkylsulfonates, arylsulfonates, halides, phosphates, carbonates, alkylphosphates, alkylcarbonates, nitrate, alkoxides, tetrafluoroborate or perchlorate.

Additionally useful as conductive salts are the acids derived from the aforementioned anions, i.e., for example, sulfuric acid, sulfonic acids and carboxylic acids.

Additionally suitable as conductive salts are also ionic liquids. Suitable ionic liquids are described in "Ionic Liquids in Synthesis", editors Peter Wasserscheid, Tom Welton, publisher: Wiley VCH, 2003, ch. 1 to 3, and in DE-A 102004011427.

Preferred conductive salts in the process according to the invention are methyltributylammonium methylsulfate, methyltriethylammonium methylsulfate, sodium methylsulfonate, sodium ethylsulfonate and sulfuric acid, especially preferably sodium methylsulfonate, methyltributylammonium methylsulfate and methyltriethylammonium methylsulfate and/or sulfuric acid, even more preferably methyltributylammonium methylsulfate and methyltriethylammonium methylsulfate and most preferably methyltributylammonium methylsulfate. The conductive salts mentioned, especially methyltributylammonium methylsulfate and methyltriethylammonium methylsulfate, can be used alone or in the form of mixtures with one another.

In a preferred embodiment of the process according to the invention, the conductive salt used is methyltributylammonium methylsulfate and/or methyltriethylammonium methylsulfate. Especially preferably, the conductive salt used is methyltributylammonium methylsulfate. Preference is given in turn to using the conductive salts mentioned alone or in the form of a mixture of two different conductive salts, but they are preferably used alone.

In an advantageous embodiment of the process according to the invention, the concentration of the conductive salt in the electrolysis solution is selected within the range from 0.1 to 20 percent by weight (% by weight), preferably in the range from 0.2 to 15% by weight, even more preferably from 0.25 to 10% by weight, even more preferably from 0.5 to 7.5% by weight and especially preferably in the range from 1 to 5% by weight. In a very particularly preferred embodiment of the process according to the invention, the conductive salt used is methyltributylammonium methylsulfate, methyltriethylammonium methylsulfate and/or sulfuric acid, preferably methyltributylammonium methylsulfate, and the concentration of the conductive salt in the electrolysis solution is selected within the range from 0.1 to 20 percent by weight (% by weight).

In a further preferred embodiment of the process according to the invention, the electrochemical anodic methoxylation is performed at a temperature of the electrolysis solution in the range from 35 to 70° C., preferably in the range from 45 to 60° C.

In addition, the process according to the invention is preferably performed in such a way that the electrochemical anodic methoxylation is performed at an absolute pressure in the range from 500 to 100 000 mbar, preferably at an absolute pressure in the range from 1000 to 4000 mbar.

Optionally, further customary solvents (cosolvents) are added to the electrolysis solution. These are the inert solvents which are generally customary in organic chemistry and have a high oxidation potential. Examples include dimethyl carbonate or propylene carbonate. In a preferred embodiment, the process according to the invention is therefore performed in the presence of dimethyl carbonate and/or propylene carbonate as cosolvents.

In principle, water is also suitable as a cosolvent; the proportion of water in the electrolyte is preferably less than 20% by weight.

In a particularly preferred embodiment of the process according to the invention, a) the electrochemical anodic methoxylation is performed with at least one of the compounds of the formulae (IIa), (IIb) and/or (III)

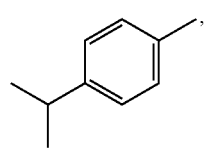
(IIa)

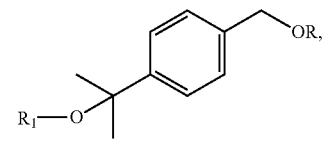
(IIb)

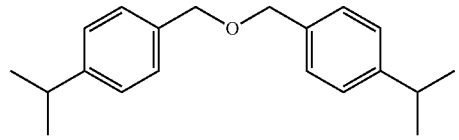
(III)

to form the corresponding diacetals of the formulae (IVa) and (IVb)

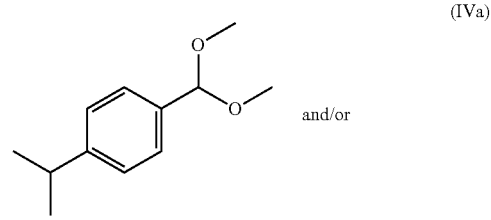
(IVa) and/or

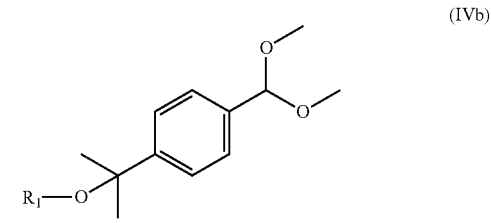
(IVb)

where $R_1$ in formula (IIb) and in formula (IVb) is a straight-chain or branched alkyl radical having 1 to 6 carbon atoms, and R in formula (IIb) is methyl or —C(O)R', and R' is a straight-chain or branched alkyl radical having 1 to 6 carbon atoms, b) the diacetals of the formulae (IVa) and/or (IVb) are hydrolyzed to form the aldehydes of the formulae (Va) and/or (Vb)

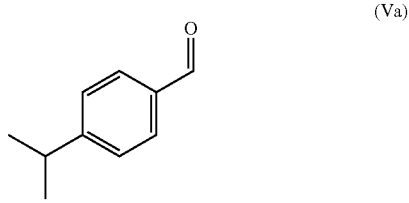
(Va)

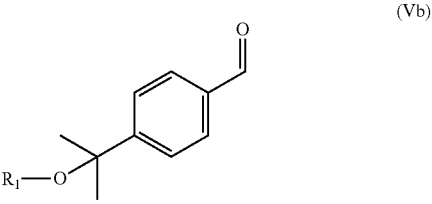
(Vb)

where $R_1$ is a straight-chain or branched alkyl radical having 1 to 6 carbon atoms, and c) the mixture of the aldehydes of the formulae (Va) and (Vb) is hydrogenated to 4-isopropylcyclohexylmethanol of the formula (I) in the presence of hydrogen or a hydrogenous gas over a catalyst which comprises, as an active metal, at least one noble metal of group VIII of the periodic table on a support, preferably ruthenium on a support which preferably comprises silicon dioxide or aluminum oxide, and most preferably silicon dioxide.

The electrochemical stage of the process according to the invention can be performed in all customary divided or undivided electrolysis cell types. It can be performed with good success either batchwise or continuously. In a preferred embodiment, electrochemical anodic methoxylation is performed continuously. Preference is given to working continuously with undivided flow cells.

Very particularly suitable are bipolar capillary gap cells or plate stack cells, in which the electrodes are configured as plates and are in a plane-parallel arrangement (Ullmann's Encyclopedia of Industrial Chemistry, 1999 electronic release, Sixth Edition, VCH-Verlag Weinheim, Volume Electrochemistry, Chapter 3.5 special cell designs and Chapter 5, Organic Electrochemistry, Subchapter 5.4.3.2 Cell Design). Preferred electrode materials are noble metals such as platinum, mixed oxide electrodes such as RuOxTiOx (known as DSA electrodes) or carbon-containing materials such as graphite, glassy carbon or diamond electrodes. Very particular preference is given to using graphite electrodes. In a preferred embodiment, the process according to the invention is performed continuously using a plate stack cell.

The current densities at which the process is performed are generally 1 to 1000 mA/cm², preferably 10 to 100 mA/cm². The process is more preferably performed at current densities between 10 and 50 mA/cm². In general, standard pressure is employed. Higher pressures are preferably employed when the intention is to work at relatively high temperatures, in order to prevent boiling of the starting compounds or of the solvent.

Suitable anode materials are, for example, noble metals such as platinum, or metal oxides such as ruthenium or chromium oxide, or mixed oxides of the $RuO_x$, $TiO_x$ type, and diamond electrodes. Preference is given to graphite or carbon electrodes.

Useful cathode materials include, for example, iron, steel, stainless steel, nickel or noble metals such as platinum, and also graphite or carbon materials and diamond electrodes. Preference is given to the system with graphite as the anode and cathode, and that with graphite as the anode and nickel, stainless steel or steel as the cathode.

In a particularly preferred embodiment of the process according to the invention, the electrochemical anodic methoxylation is performed at a temperature of the electrolysis solution in the range from 35 to 70° C., at an absolute pressure in the range from 500 to 100 000 mbar and at a current density in the range from 10 to 100 mA/cm².

After the reaction has ended, the electrolyte solution is worked up by general separating methods. For this purpose, the electrolysis solution is generally first distilled and the individual compounds are obtained separately in the form of different fractions. A further purification can be effected, for example, by crystallization, extraction, distillation or chromatography.

A further aspect of the present invention relates to a process for preparing the mixture of cuminaldehyde of the formula (Va) and 4-(1-alkoxy-1-methylethyl)benzaldehyde (alkoxycuminaldehyde) of the formula (Vb) in which $R_1$ is a straight-chain or branched alkyl radical having 1 to 6 carbon atoms

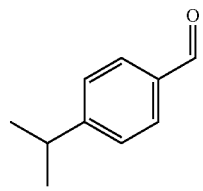

(Va)

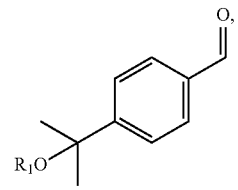

(Vb)

comprising the steps of anodic methoxylation of paracymene of the formula (IIa) and/or of 4-isopropylbenzyl compounds of the formula (IIb), in which R and $R_1$ are each as defined in formula (IIb), and/or the di(4-isopropylbenzyl) ether of the formula (IIIa) and/or the di(4-isopropylbenzyl) ether of the formula (IIIb) in an electrolysis solution comprising methanol, at least one conductive salt and optionally a further solvent or a plurality of different solvents, performed in such a way that a mixture of the dimethyl diacetals of the formula (IVa) and of the formula (IVb) is formed

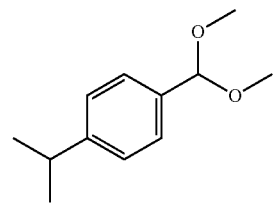

(IVa)

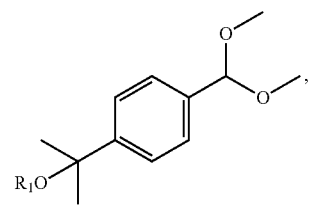

(IVb)

in which $R_1$ is a straight-chain or branched alkyl radical having 1 to 6 carbon atoms, and subsequent hydrolysis to form a mixture of the aldehydes of the formulae (Va) and (Vb).

The hydrolysis mentioned can generally be accomplished by processes known per se to the person skilled in the art, for example by simple contacting of the compound of the formula (IV), especially of the formulae (IVa) and (IVb), with water or an acid, for example dilute hydrochloric acid, sulfuric acid or else acetic acid.

In a particularly preferred embodiment of the process according to the invention, the mass ratio of the two aldehydes of the formulae (Va) and (Vb) is between 0.2 and 10.

In a further aspect, the present invention relates to 4-(1-alkoxy-1-methylethyl)benzaldehyde dimethyl acetal of the formula (IVb)

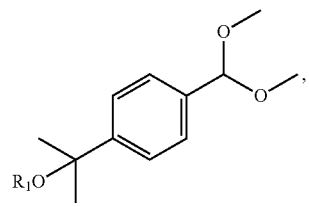

(IVb)

in which R₁ is a straight-chain or branched alkyl radical having 1 to 6 carbon atoms.

In a further aspect, the present invention finally relates to the compound of the formula (IX) passed through as an intermediate

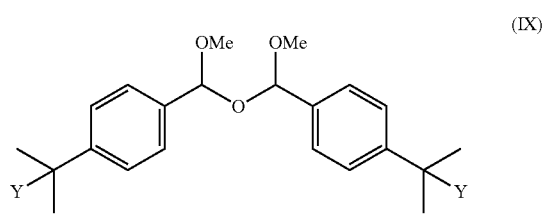

(IX)

in which Me is methyl and Y is hydrogen or the —OR₁ radical, where R₁ is a straight-chain or branched alkyl radical having 1 to 6 carbon atoms.

The invention is illustrated in detail by the examples which follow, without restricting it thereto. The abbreviation DM water means demineralized water.

EXAMPLE 1

Preparation of a Mixture of Cuminaldehyde and Methoxycuminaldehyde of the Formulae (Va) and (Vb)

Apparatus: An undivided capillary gap cell (plate stack cell) with 18 round graphite electrodes, material: MKUS F04 (SGL Carbon, Meitingen, Germany), with a gap width of 1 mm was used.

Electrolyte: 600 g (4.47 mol, 20% by weight) of p-cymene and 100 g of methyltributylammonium methylsulfate (MTBS conductive salt) (60% solution in methanol, 2% by weight) in 2300 g of methanol, corresponding to a batch size of 3000 g, were converted.

Conditions: The electrolysis was effected at a current density of 3.4 A/cm², a voltage (per gap) of 4.4-6.1 V, and a temperature of 57° C. An amount of charge of up to 15 F/mol of p-cymene was passed through the cell.

The gas chromatography evaluation (30 m DB-1, 80°/5'/ 8°/250°) of the electrolysis output gave the following result:

| Substance (retention time in min.) | GC area percent |
|---|---|
| Low boilers (to 6.90): | 48.5 (in total) |
| Cumin dimethyl acetal (IVa) (19.35) | 13.9 |
| Cumin ester (19.50) | 1.8 |
| Methoxycumin ether (IIe) (20.10) | 0.19 |

| Substance (retention time in min.) | GC area percent |
|---|---|
| Cumin orthoester (21.20) | 0.55 |
| Methoxycumin acetal (IVb) (22.30) | 29.2 |
| Methoxycumin ester (22.45) | 0.20 |
| Methoxycumin orthoester (23.85) | 0.23 |
| Others, high boilers, dimers | 5.44 (in total) |

For workup, the cell was purged with methanol. The purged methanol was combined with the electrolysis output, a pH of 7-8 was established with sodium methoxide (30% solution) and methanol was distilled off. The residue was fractionally distilled on a 30 cm silver mirror column with random packing:

Mass balance from the distillation: 219 g (1.13 mol) of cumin acetal of the formula (IVa) (proportion by mass=25%) and 471 g (2.10 mol) of methoxycumin acetal of the formula (IVb) (proportion by mass=47%).

EXAMPLE 2

Hydrolysis of Methoxycumin Acetal 1395 g of methoxycumin acetal (IVb) (distilled, purity 93.8 GC %, 7.34 mol) were heated to reflux in a 4 l stirred apparatus with a Pt-100 temperature sensor and Normag column head with 1674 g of DM water for 2 h. The mixture was allowed to cool to room temperature and the phases were separated. The aqueous phase was extracted twice with tert-butyl methyl ether (MTBE) and the combined organic phases were freed of the solvent.

Distillation of the crude product (T(bottom)=132-136° C.; T(distillation)=98° C.; p=3 mbar) on a 30 cm silver mirror column with random packing gives methoxycuminaldehyde (Vb) in 90% yield and up to 99.2% purity (by GC).

EXAMPLE 3

Hydrogenation of Methoxycuminaldehyde of the Formula (Vb)

A 300 ml pressure reactor was initially charged with 3.5 g of a catalyst prepared according to DE102005029200A1 in a catalyst insert basket, which were admixed with 20 g of methoxycuminaldehyde (formula (Vb)) (in 80 g of tetrahydrofuran (THF); 20% by weight). The hydrogenation was performed with pure hydrogen (purity≥99.99% by volume) at a constant pressure of 200 bar and a temperature of 160° C. Hydrogenation was continued until no further hydrogen was taken up (20 hours). The reactor was subsequently decompressed. The conversion of methoxycuminaldehyde (formula (Vb)) was 100%; the 4-(1-methoxy-1-methylethyl)cyclohexylmethanol intermediate was detectable by gas chromatography at 28.8% in the starting mixture (GC column: DB-wax, length 30 m, layer thickness 0.25 µm; temperature program: from 60° C. at 2.5° C./min to 240° C.). The selectivity of 4-isopropylcyclohexylmethanol (IPCHM) was 33 area %; the ratio of cis-IPCHM (Ia) to trans-IPCHM (Ib) was 1.6. The secondary components detected were approx. 22 area % of low boilers (components with a lower boiling point than 4-isopropylcyclohexylmethanol).

EXAMPLE 4

Hydrogenation of a Mixture of Cuminaldehyde (Va) and Methoxycuminaldehyde (Vb)

A 300 ml pressure reactor was initially charged with 3.5 g of a catalyst prepared according to DE102005029200A1 in a catalyst insert basket, which were admixed with 20 g of methoxycuminaldehyde (formula Vb)/cuminaldehyde (formula Va) in 90% purity in a ratio of 1:1 (in 80 g of THF; 20% by weight). The hydrogenation was performed with pure hydrogen at a constant pressure of 200 bar and a temperature of 180° C. Hydrogenation was effected for 15 hours. The reactor was subsequently decompressed. The output was analyzed by gas chromatography (GC column: DB-Wax, length 30 m, layer thickness 0.25 μm; temperature program: from 60° C. at 2.5° C./min to 240° C.). It had the following composition (GC area %):
Low boilers: 31.1%
Isopropylcyclohexylmethanol: 60.2%
Methoxyisopropylcyclohexylmethanol: 5.5%
Methoxycumin alcohol: 1.6%.

EXAMPLE 5

Hydrogenation of a Mixture of Cuminaldehyde (Va) and Methoxycuminaldehyde (Vb)

A 300 ml pressure reactor was initially charged with 4.5 g of a catalyst prepared according to DE102005029200A1 in a catalyst insert basket, which were admixed with 100 g of methoxycuminaldehyde (formula Vb)/cuminaldehyde (formula Va) in 90% purity in a ratio of 1:1. The hydrogenation was performed with pure hydrogen at a constant pressure of 200 bar and a temperature of 180° C. Hydrogenation was effected for 24 hours. The reactor was subsequently decompressed. The output was analyzed by gas chromatography (GC column: DB-Wax, length 30 m, layer thickness 0.25 μm; temperature program: from 60° C. at 2.5° C./min to 240° C.). It had the following composition (GC area %):
Low boilers: 35.8%
Isopropylcyclohexylmethanol: 38.1%
Isopropylbenzyl alcohol: 7.8%
Methoxyisopropylcyclohexylmethanol: 1.4%
Methoxycumin alcohol: 1.1%.

The invention claimed is:
1. A process for preparing 4-isopropylcyclohexylmethanol of the formula (I)

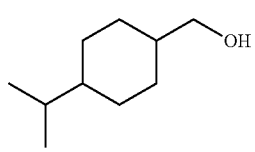

(I)

comprising the steps of
a) electrochemical anodic methoxylation is performed with at least two compounds of the formulae (IIa), (IIb), (IIIa) and/or (IIIb)

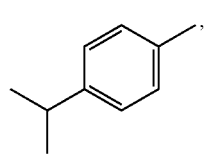

(IIa)

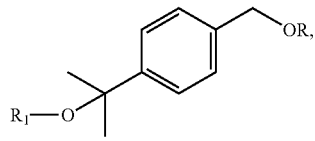

(IIb)

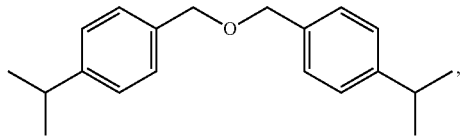

(IIIa)

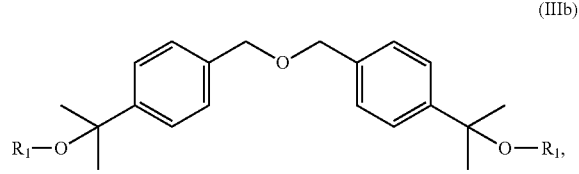

(IIIb)

such that a mixture of the diacetals of the formulae (IVa) and (IVb)

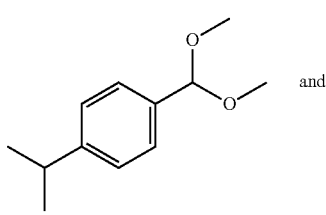

(IVa)

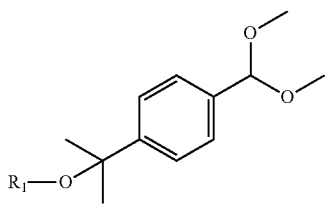

(IVb)

is formed, where $R_1$ in the formulae (IIb), (IIIb) and (IVb) is a straight-chain or branched alkyl radical having 1 to 6 carbon atoms, and R in formula (IIb) is methyl or —C(O)R', and R' is a straight-chain or branched alkyl radical having 1 to 6 carbon atoms,
b) hydrolysing the mixture of the diacetals of the formulae (IVa) and/or (IVb) to form the aldehydes of the formulae (Va) and/or (Vb)

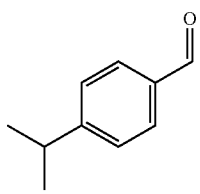

(Va)

-continued (Vb)

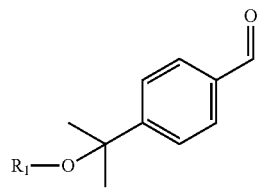

where $R_1$ is a straight-chain or branched alkyl radical having 1 to 6 carbon atoms, and c) hydrogenating the mixture of the aldehydes of the formulae (Va) and (Vb) to 4-isopropylcyclohexylmethanol of the formula (I) in the presence of hydrogen or a hydrogenous gas over a catalyst which comprises, as an active metal, at least one noble metal of group VIII of the periodic table on a support.

2. The process of claim 1, wherein the noble metal of group VIII of the periodic table used is ruthenium.

3. The process of claim 1, wherein the support comprises silicon dioxide.

4. The process of claim 1, wherein the electrochemical anodic methoxylation is performed in the presence of the compound of the formula (IIa)

(IIa)

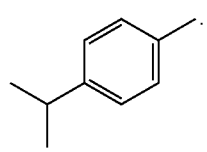

5. The process of claim 1, wherein a conductive salt used is methyltributylammonium methylsulfate, methyltriethylammonium methylsulfate and/or sulfuric acid, and the concentration of the conductive salt in an electrolysis solution is selected within the range from 0.1 to 20 percent by weight (% by weight).

6. The process of claim 1, which further comprises a solvent wherein the solvent is dimethyl carbonate or propylene carbonate, or a mixture of these solvents.

7. The process of claim 5, wherein the electrochemical anodic methoxylation is performed at a temperature of the electrolysis solution in the range from 35 to 70° C., at an absolute pressure in the range from 500 to 100 000 mbar and at a current density in the range from 10 to 100 mA/cm².

8. The process of claim 1, wherein the electrochemical anodic methoxylation is performed continuously and using a plate stack cell.

9. A process for preparing a mixture of 4-isopropylbenzaldehyde of the formula (Va)

(Va)

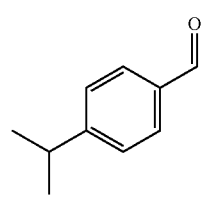

and of alkoxycuminaldehyde of the formula (Vb)

(Vb)

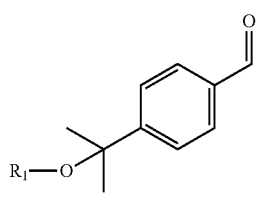

in which $R_1$ is an alkyl radical having 1 to 6 carbon atoms, comprising the steps of a) electrochemical anodic methoxylation of para-cymene of the formula (IIa)

(IIa)

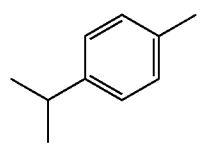

and/or of 4-isopropylbenzyl compounds of the formula (IIb)

(IIb)

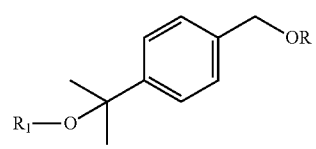

in which R is methyl or C(O)R', and where R' and $R_1$ are each independently a straight-chain or branched alkyl radical having 1 to 6 carbon atoms,
and/or of the di(4-isopropylbenzyl)ether of the formula (IIIa)

(IIIa)

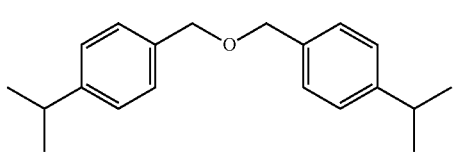

and/or of the di(4-isopropylbenzyl)ether of the formula (IIIb)

(IIIb)

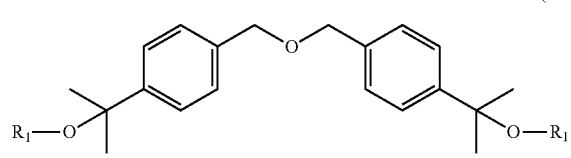

in which $R_1$ in formula (IIIb) is as defined in formula (IIb), in an electrolysis solution comprising methanol, at least one conductive salt and optionally a further solvent or a plurality of different solvents, and wherein the electrochemical anodic methoxylation is performed such that a mixture of the dimethyl diacetals of the formulae (IVa) and (IVb) is formed

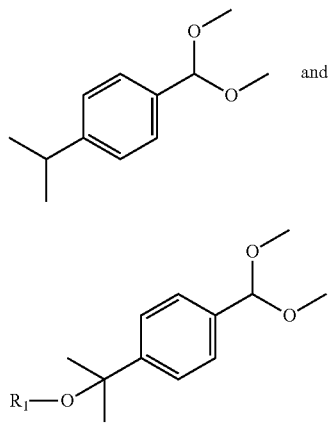

(IVa)

and (IVb)

b) hydrolysis of the dimethyl diacetals of the formulae (IVa) and (IVb) to form a mixture of the aldehydes of the formulae (Va) and (Vb).

10. A compound of the formula (IX)

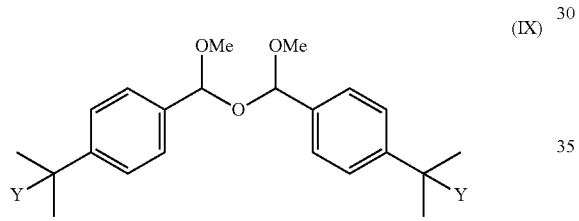

(IX)

where Me is methyl and Y is hydrogen or the —O—R$_1$ radical where R$_1$ is a straight-chain or branched alkyl radical having 1 to 6 carbon atoms.

11. The process of claim 1, wherein, apart from the aldehydes of the formulae (Va) and (Vb) where R1 is methyl, it is also possible to use the corresponding alcohols 4-isopropylbenzyl alcohol and 4-(1-methoxy-1-methylethyl)benzyl alcohol.

12. The process of claim 1, wherein the mass ratio of the two aldehydes of the formulae (Va) and (Vb) is between 0.2 and 10.

13. The process of claim 1, wherein the hydrogenation is performed at a temperature of 80-200° C.

14. The process of claim 1, wherein the hydrogenation with hydrogen is performed at a total pressure of 100-200 bar.

15. The process of claim 1, wherein a fixed bed catalyst which, based on the total weight of the finished catalyst, has an active content, of 0.1 to 0.5% by weight is used.

16. The process of claim 1, wherein the active metal used in the hydrogenation is at least one noble metal of group VIII of the periodic table, either alone or together with at least one further metal of transition groups IB, VIIB or VIII of the periodic table of the elements, applied to a support comprising silicon dioxide as a support material, where the amount of the active metal is <1% by weight, based on the total weight of the catalyst, and at least 60% by weight of the active metal is present in the shell of the catalyst down to a penetration depth of 200 μm.

17. The process of claim 1, wherein the 4-isopropylcyclohexylmethanol has a ratio of cis-4-isopropylcyclohexylmethanol (Ia) to trans-4-isopropylcyclohexylmethanol (Ib) is greater than 1.9

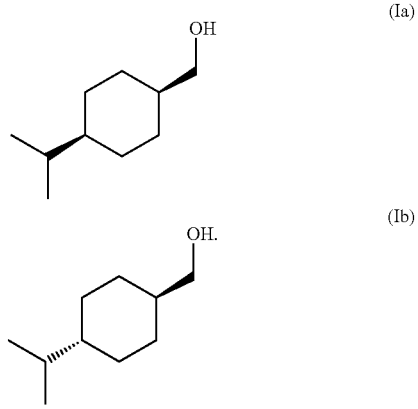

(Ia)

(Ib)

18. The process of claim 1, wherein the hydrogenation is performed at a temperature of 120 and 160° C. and wherein a fixed bed catalyst which, based on the total weight of the finished catalyst, has an active ruthenium content, of 0.1 to 0.5% by weight is used.

19. The process of claim 16, wherein the active metal used is rhodium and ruthenium.

* * * * *